United States Patent [19]
Klicker

[11] Patent Number: 5,729,520
[45] Date of Patent: Mar. 17, 1998

[54] INSPECTION OF AN OPTICAL DISC WITH A LIGHT BEAM WHICH IS REFLECTED BY THE DISC AND EXPOSED TO TWO PHOTOSENSITIVE RECEIVERS

[75] Inventor: Jürgen Klicker, Hoisdorf, Germany

[73] Assignee: Basler GmbH, Ahrensburg, Germany

[21] Appl. No.: 531,693

[22] Filed: Sep. 21, 1995

[30] Foreign Application Priority Data

Sep. 27, 1994 [DE] Germany ............... 44 34 474.0

[51] Int. Cl.$^6$ ............................................. G11B 7/125
[52] U.S. Cl. ........................... 369/112; 369/54; 369/58; 369/110
[58] Field of Search ........................ 369/112, 54, 58, 369/57, 109, 110, 122; 250/201.5; 356/394, 386, 446

[56] References Cited

U.S. PATENT DOCUMENTS

| | | | |
|---|---|---|---|
| 4,030,835 | 6/1977 | Firester et al. | 356/111 |
| 4,841,510 | 6/1989 | Yoshizawa | 369/46 |
| 4,941,138 | 7/1990 | Childs et al. | 369/50 |
| 5,131,755 | 7/1992 | Chadwick et al. | 356/394 |
| 5,475,667 | 12/1995 | Kamimura et al. | 369/54 |

FOREIGN PATENT DOCUMENTS

| | | |
|---|---|---|
| 3515602 | 11/1986 | Germany. |
| 3641863 | 6/1988 | Germany. |
| 3717274 | 12/1988 | Germany. |
| 2312028 A | 12/1990 | Japan. |
| 3269842 A | 12/1991 | Japan. |

*Primary Examiner*—David C. Nelms
*Assistant Examiner*—Kim-Kwok Chu
*Attorney, Agent, or Firm*—Howson and Howson

[57] ABSTRACT

The invention pertains to a method and a device for carrying out the quality control of an object (10) that comprises at least one transparent layer (18). According to this method and this device, at least one light beam (41) of a light source (42) is projected onto the object (10) at an angle (α) and is received by at least one photosensitive receiver (53). According to the invention, it is proposed that the light beam (48) that emerges from the object be split before it is projected onto the first photosensitive receiver (53), with part of the light beam being deflected in the direction toward a second photosensitive receiver (62). This measure makes it possible to expose simultaneously two different photosensitive receivers (53, 62) so as to display different defects of an object (10).

18 Claims, 5 Drawing Sheets

INSPECTION OF AN OPTICAL DISC WITH A LIGHT BEAM WHICH IS REFLECTED BY THE DISC AND EXPOSED TO TWO PHOTOSENSITIVE RECEIVERS

BRIEF SUMMARY OF THE INVENTION

The invention pertains to a method and a device for carrying out the quality control of an object that has at least one transparent layer. According to this method and this device, at least one light beam of a light source is projected onto the object at an angle and the light beam that emerges from the object is received by at least one photosensitive receiver. The light beam can, in principle, be reflected by a reflective layer of the object which is arranged behind the transparent layer or pass through the object, i.e., the photosensitive receiver either receives a reflected light beam or a light beam that has passed through the object. For reasons of simplicity, the following description simply refers to a light beam that is reflected by the object, passes through the object or emerges from said object. The invention in particular pertains to the optical quality control of a compact disc (CD), i.e., the following description primarily refers to a CD, but the invention is not limited to this particular type of application.

Lately CDs have become more and more popular because these sound carriers produce a very high sound quality in domestic use. However, they are also used as pure data carriers for data processing systems because of their high data density. Last but not least, the relative insensitivity to external influences represents one additional reason for the continued popularity of CDs. Consequently, a CD unquestionably represents a mass-produced product which, however, needs to fulfill the strictest quality requirements.

There exist numerous methods for measuring the different defects that can occur during the manufacture of a CD. Due to the physical design of a CD, i.e., a transparent layer with a reflective layer arranged behind it, optical measuring methods and measuring devices which are also the object of this invention are particularly suitable for this purpose.

The initial description pertains to the design and the manufacture of a CD as well as the possible defects that can occur during the manufacturing process. A CD consists of a circular disk, in the center of which an aperture is arranged for centering it in a CD player. Viewed from the bottom, i.e., the reading side of the CD player, toward the top, the cross section of this disk consists of a transparent plastic layer that is generally manufactured of polycarbonate and contains all information in the form of pits. A metal layer that usually consists of aluminum and serves for rendering the surface of the polycarbonate layer reflective is arranged on top of the aforementioned transparent plastic layer such that the information can be read by the optical scanning system of the CD player. This very thin metal layer is protected by a coat of lacquer that is also very thin and usually hardened by means of UV light. Lettering or the like can be arranged on this coat of lacquer in order to label the CD.

Viewed in the radial direction, a CD has several concentric, annular regions that originate from the central aperture and extend outward. The region that serves for clamping the CD in the CD player is situated directly on the central aperture. A region that carries the so-called identification code that serves for conclusively identifying the CD is situated adjacent to the aforementioned region. The region that serves for storing the data is situated adjacent to the region carrying the identification code. If the CD is prerecorded to its maximum storage capacity, this region ends directly at the outer border region. Otherwise, the so-called lead-out or an image band is arranged between the outer edge region of the CD and the data region.

When manufacturing a CD, a blank is initially manufactured of polycarbonate by means of die-casting, with all information already being impressed by means of the die plate. Subsequently, one surface of the blank is provided with the metallic reflective layer by means of sputtering and sealed with the coat of lacquer. The CD is centrifuged during these processes in order to realize the uniform distribution of the aluminum layer and the coat of lacquer and to obtain the thinnest possible layer. Subsequently, the label is printed onto the CD.

It is obvious that the reflective layer and the transparent polycarbonate body need to be flawless with respect to their optical properties due to the high data density of the CD that is read in an optical fashion. The slightest defects, in particular within the data region, can cause significant interference during the reading process, i.e., unacceptable aberrations can result, in particular if the CD is used for data processing. Consequently, it is practical as well as necessary to incorporate a quality control that makes it possible to detect and classify the possible defects of a CD into the production process such that a subsequent elimination of the defective CDs or a rectification of the production process can be carried out.

The following defects can occur: holes in the reflective layer, so-called pinholes, are created by a dust particle or the like which is present on the surface before the sputtering process and are thrown outward while entraining a piece of the metallic surface during the centrifuging of the CD. Aluminum scratches occur if the dust particle remains on the surface while it is thrown outward and consequently causes additional damage to the metal layer. Underneath the metal layer, organic residues, e.g., oil stains, can lead to scanning errors. So called pimple defects are created if the polycarbonate blank is deformed on the side that is to be coated. Inclusions of foreign matter in the polycarbonate layer are called black spots. Bubbles, air inclusions or the like can also be present in the polycarbonate layer. In addition, the underside of the CD can contain lacquer splashes or scratches that are caused by mechanical influences and lead to reading errors or diminish the sound quality.

Depending on their size, these defects always cause optical aberrations that can usually be detected with conventional test equipment. However, a classification of the defects also requires that the depth of the respective defects is determined. Consequently, it is required to utilize measuring methods and measuring devices that are able to measure the defects in a three-dimensional fashion. Depending on the data density, it is, at least within the data region, also required to carry out the tests with a high inspection level, i.e., a local resolution within the range between 30 µm and 50 µm needs to be attained. Outside of the data region, only defects that influence the optical appearance of the CD are important. In this case, a lower inspection level, e.g., with a local resolution of approximately 200 µm which corresponds to that of the human eye, would suffice.

In addition, optical distortions in the CD can be caused, for example, due to a convex or concave deformation of the CD. Internal stresses in the polycarbonate layer also lead to reading errors because polycarbonate is an optically active material under tension, i.e., birefrigence occurs. This causes the usually polarized light of the scanning laser in the CD player to be subjected to an undesired change in polarization due to this accidental birefrigence. In addition, defects in the microstructure of the polycarbonate layer frequently lead to reading errors. The reason for these so-called clouds frequently lies in the die plate, i.e., one must assume that the system does not operate properly if such a cloud is present.

In order to detect the first-mentioned group of defects, there exist measuring methods and measuring devices in which a linear light beam is projected onto the underside at an acute angle, reflected and received by a so-called line camera. The defect appears in the camera in the form of a dark spot. The CD carries out one revolution during the test procedure such that the entire CD can be illuminated and examined as to the presence of possible defects. Due to the distinct geometry and the predetermined revolution of the CD, one can simultaneously draw conclusions as to the depth of a defect since the same defect appears twice at the same location during the revolution, i.e., because said defect lies in the incident light beam as well as in the emerging light beam. However, it is currently not possible to reliably detect the presence of a cloud with conventional measuring methods.

In order to detect internal stresses, the light beam is polarized in linear fashion via a polarizing filter behind the light source, with a linear polarizing filter also being arranged in front of the camera. The polarizing filters are usually arranged in such a way that they are turned relative to one another by 90°. When testing a flawless CD, i.e., a CD without internal stresses, the camera remains completely dark because the polarized light did not change while passing through the polycarbonate layer. Otherwise, the brightness observed in the camera represents a measure of the internal stresses.

Deformations of a CD are determined by projecting a point source light beam that in most cases originates from a semiconductor light source onto the underside of the CD and reflecting said light beam in the direction of a position-sensitive photodiode. Photodiodes of this type can, for example, be realized in the form of four-quadrant diodes. When testing a flat CD, the light beam is reflected onto a certain region of the photodiode. When testing a CD that is deformed in convex or concave fashion, for example, the light beam is deflected and illuminates a different quadrant of the photodiode. In this case, the extent of the deflection can be used as a measure of the extent of the deformation. However, one disadvantage of this method can be seen in that the CD is only tested along one diameter. Hat-shaped or bead-shaped deformations cannot be detected if the light beam is projected onto an otherwise flat CD.

It is obvious that a total of three measuring methods is required for carrying out a comprehensive test of a CD. This is quite time-consuming and consequently cannot be easily incorporated into a production process. In addition, the test benches required for this purpose are associated with increased mechanical expenditures. One additional disadvantage of known test methods can be seen in the fact that it is not possible to reliably detect and identify all types of defects.

The invention is based on the objective of developing a measuring method and a measuring device which make it possible to detect at least a large number of the known defects in a single step.

According to the invention, this objective is attained due to the fact that the light beam that emerges from the object is split before it is projected onto the photosensitive receiver, and that a portion of the light beam is deflected in the direction toward a second photosensitive receiver. This measure provides the advantage that two photosensitive receivers are simultaneously exposed by only one light beam. It is, for example, possible to utilize two different types of cameras that would be particularly practical for displaying only one or the other type of defect in one step of the method for carrying out the quality control of a CD. Consequently, it is possible to simultaneously display different types of defects that require different photosensitive receivers.

At this point it should be mentioned that the description refers to the display of a defect on or by the photosensitive receiver, i.e., the defect is recorded by the photosensitive receiver and graphically illustrated on a corresponding display device, e.g., a monitor that is connected to the photosensitive receiver.

According to one embodiment example, it is proposed that the light beam that emerges from the object be split by a beam splitter that is arranged between the first photosensitive receiver and the object. This measure makes it possible to attain a simple design of the device required for carrying out the quality control.

According to another embodiment of the invention, it is proposed that the light beam that emerges from the object be reflected by a partially transparent mirror before said light beam is projected onto the first photosensitive receiver, namely in such a way that the light beam reflected at this location is projected onto the object in the opposite direction at an angle that essentially is identical to the angle of incidence, reflected and projected onto a beam splitter that is arranged between the object and the light source, with part of the light beam being deflected in the direction toward the second photosensitive receiver inside of said beam splitter. This progression of the light beam provides the advantage that the contrast at the second photosensitive receiver can be increased because the incident light beam, as well as the light beam reflected by the partially transparent mirror, passes over the object, e.g., a CD, while said object remains in the same position, i.e., the object does not revolve. Consequently, defects that have a lower contrast, e.g., large-surface or random defects that only cause a minute diminishing of the light beam if it passes over the object once, can also be detected because these defects now decrease the light beam twice.

According to another embodiment of the invention, it is proposed that the light beam be polarized behind the light source. According to an additional development of this embodiment, it is proposed that at least one wavelength range of the light beam be circularly or elliptically polarized after the light source. It was unexpectedly demonstrated that circularly or elliptically polarized light makes possible superior visibility of the defects in the microstructure, namely the so-called clouds, on the photosensitive receiver and allows a distinct classification of said defects. Consequently, it is possible to display these defects on one of the photosensitive receivers. Possibly damaged die plates can be detected immediately, i.e., it is, for example, possible to carry out an immediate correction of the current production process so as to keep the amount of waste to a minimum.

It is particularly advantageous if the portion, the polarization type of which corresponds to the polarization type of the emitted light, is filtered out of the light beam before it is projected onto at least one photosensitive receiver. This measure makes it possible to also display internal stresses on the corresponding photosensitive receiver. If the light is polarized in a linear fashion, this can be realized by arranging a linear polarizing filter in front of the corresponding photosensitive receiver.

If the emitted light is circularly or elliptically polarized, a phase delay plate, e.g., a λ/4 plate, as well as a linear polarizing filter are arranged in front of the photosensitive receiver viewed in the beam direction. The utilization of circularly polarized light provides the advantage that the birefrigence caused by internal stresses can be detected in a superior fashion independently of the privileged direction. Possible, this birefrigence cannot be detected with only linearly polarized light. In this case, the phase delay plate in front of the photosensitive receiver has the same wavelength range as the phase delay plate behind the light source, i.e., both phase delay plates are functional at the same wavelength. The utilization of elliptically polarized light provides the advantage that changes in polarization which are caused by the reflection on the reflective metal layer can be compensated.

In addition, it is practical to align the polarizing device in front of the corresponding photosensitive receiver in such a way that the light is able to pass if the tested object does not exhibit any birefrigence. This measure makes it possible to display two defect phenomena on one photosensitive receiver. In addition to the internal stresses, it is, for example, possible to display the deformation by means of a matrix camera. If the polarization is changed due to the birefrigence caused by the internal stress, the photosensitive receiver would remain entirely or partially dark at least within this region.

According to one embodiment example of the invention, it is proposed that the wavelength range which corresponds to the wavelength range of the circularly or elliptically polarized emitted light, be filtered out before it is projected onto at least one photosensitive receiver. This measure makes it possible to increase the measuring accuracy as well as the contrast.

It is practical if the light beam illuminates the object in a linear fashion. In this case, at least one photosensitive receiver can be realized in the form of a line camera. However, it is also possible to realize at least one photosensitive receiver in the form of a matrix camera. This measure simplifies the testing of a CD because the CD can be illuminated by radially extending beams.

According to one additional embodiment of the invention, it is proposed that the measurements be carried out while the object carries out at least one complete revolution, with at least part of the measured values being evaluated in an electronic data processing system so as to generate an essentially complete image of the tested object. This measure simplifies and accelerates the comprehensive measurements.

It is also possible to carry out the test of the object with different inspection levels within different regions of the object. This measure reduces the time required for the evaluation process because the data quantity is directly dependent on the inspection level, and a reduction of said inspection level, even if only in one or the other region, causes a reduction in the amount of data and consequently in computing time.

In addition, it is practical if the different regions of the object are identified with the aid of the different gray scale values of the light recorded within these regions. The identification of the different regions can simply be carried out by the data processing system such that the inspection levels can be adjusted automatically in accordance with predetermined values. In this case, the test of the object can be carried out with different inspection levels within the identified regions. This measure provides the advantage that the set-up time of the test device can be additionally reduced because a manual adjustment of the different regions is eliminated. This measure in particular reduces the so-called pseudo-waste because the function of the CD remains intact in case of a defect outside the data region. A complete classification of a defect also includes an indication as to the fact within which region the defect has occurred.

In addition, it is practical if the position and the dimensions of the identified regions are measured. The respective position of the regions can, for example, be evaluated with respect to a possible eccentricity in the case of a CD. The dimensions can, for example, be used as a measure of the curvature of a CD (dishing). In this case, it is practical if the dimensions of the regions are compared to reference values.

The device for carrying out a comprehensive quality control of an object that has at least one transparent layer and a reflective layer that is arranged behind the aforementioned transparent layer and reflects the light in the direction toward the transparent layer, in particular a compact disc (CD), comprises a light source for generating at least one light beam that is projected onto the object at an angle of incidence and at least a first photosensitive receiver for receiving the reflected light beam or the light beam that has passed through the object. According to the invention, it is proposed that at least one element for splitting the light beam that emerges from the object before it is projected onto the first photosensitive receiver be provided, and that part of the light is deflected in the direction toward a second photosensitive receiver. This measure makes it possible to expose simultaneously two photosensitive receivers in a device with only one light source.

According to one embodiment, it is proposed that a beam splitter be arranged between the object and the first photosensitive receiver, and that the second photosensitive receiver be arranged in the direction of deflection of the beam splitter. This means that the light beams that emerge from the beam splitter respectively extend in the direction toward one photosensitive receiver. However, it can be particularly advantageous if a partially transparent mirror that is aligned in such a way that it reflects the light beam reflected by the object in exactly the opposite direction is provided, with a beam splitter being arranged between the light source and the object, and that the second photosensitive receiver is arranged in accordance with the direction of deflection of the beam splitter. This measure makes it possible to increase significantly the contrast of the image recorded by the second photosensitive receiver.

It can be particularly practical if at least one polarizing device is arranged between the light source and the object. In this case, it is also advantageous if a corresponding polarizing device is arranged in front of at least one photosensitive receiver. The polarizing device in front of the photosensitive receiver is able to filter that portion, whose polarization type corresponds to the polarization type of the emitted light from the light that emerges from the object. This measure makes it possible to detect internal stresses in a CD by means of a camera.

In addition, it is practical if the polarizing device comprises a linear polarizing filter and a phase delay plate, e.g., a λ/4 plate, in order to circularly or elliptically polarize at least one wavelength range of the light. This means that at least one wavelength of the emitted light is circularly or elliptically polarized such that defects in the microstructure of a CD are detected. If a corresponding polarizing device which comprises a phase delay plate and a linear polarizing filter, as viewed in the beam direction, in order to filter out the corresponding type of polarization is installed in the opposite direction in front of a photosensitive receiver, this measure also makes it possible to display internal stresses independently of the privileged direction of the birefrigence. In this case, the phase delay plate that is arranged in front of the photosensitive receiver, e.g., a λ/4 plate, has the same wavelength as the phase delay plate that is arranged after the light source, e.g., a λ/4 plate. In addition, it is advantageous if a color filter, the wavelength range of which corresponds to the wavelength range of the circularly or elliptically polarized light, is arranged in front, as viewed in the beam direction, of the polarizing device that is situated in front of the camera, i.e., in front of the phase delay plate.

In this case, the correspondingly designed polarizing devices can be aligned in such a way that the light passes if an essentially flawless object is tested, e.g., a CD without internal stresses. This measure makes it possible to utilize the image generated on the photosensitive receiver for additional evaluations.

It is practical if the corresponding polarizing device is arranged behind the beam splitter or the partially transparent mirror. This means that a corresponding polarizing device is only arranged in front of one photosensitive receiver for only a portion of the light beam. The other portion of the light beam exposes the other photosensitive receiver without being filtered such that, for example, the defects of the first-mentioned group of defects can be displayed without possibly being influenced by the display of internal stresses. It can be particularly practical if the partially transparent mirror is realized in the form of an interference filter, the wavelength of which corresponds to the wavelength of the circularly polarized light. This measure makes it possible to eliminate the color filter such that the remaining portion of the light is reflected and still exposes the second photosensitive receiver with sufficient light intensity.

According to one embodiment example of the invention, it is proposed that the light source generates a linear light beam. In this case, it is possible to realize at least one photosensitive receiver in the form of a line camera. It can also be advantageous if at least one photosensitive receiver is realized in the form of a matrix camera. A matrix camera is able to display the possible deformations of a CD in a superior fashion. If such a deformation exists, a linear illumination of the CD is displayed as a correspondingly curved line in the matrix camera that has a two-dimensional receiver. Consequently, it is also possible to detect hat-shaped or bead-shaped deformations of a CD. Naturally, it is also possible to realize one photosensitive receiver in the form of a line camera and the other photosensitive receiver in the form of a matrix camera.

It is particularly practical if the first photosensitive receiver is realized in the form of a matrix camera that is arranged after the partially transparent mirror and the second photosensitive receiver is realized in the form of a line camera.

In this case, it is practical if the corresponding polarizing device is arranged in front of the matrix camera. Such an arrangement makes it possible to display the internal stresses and the deformations in the matrix camera while the other defects, including the clouds, are displayed in the line camera. The contrast of the display of the first-mentioned defects can be additionally increased by the second photosensitive receiver in an embodiment in which the beam splitter is arranged between the CD and the light source.

In order to accelerate and automate the test procedures, at least one photosensitive receiver can be connected to a data processing system. This measure makes it possible to display a complete image of the examined CD as well as all detected defects on a monitor.

BRIEF DESCRIPTION OF THE DRAWINGS

The invention is described in detail below with reference to the schematic figures. Shown are.

DETAILED DESCRIPTION

Figure 1:
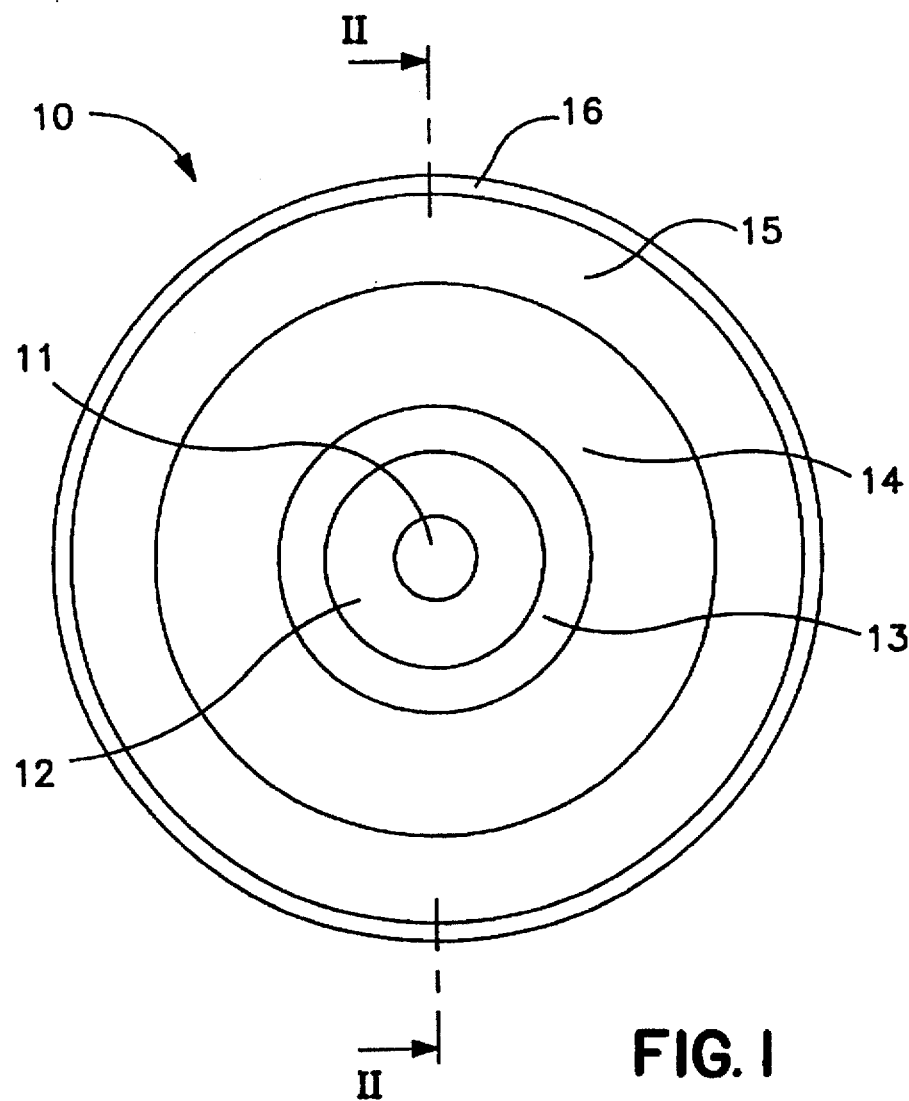
FIG. 1, a top view of a compact disc.
Figure 2:
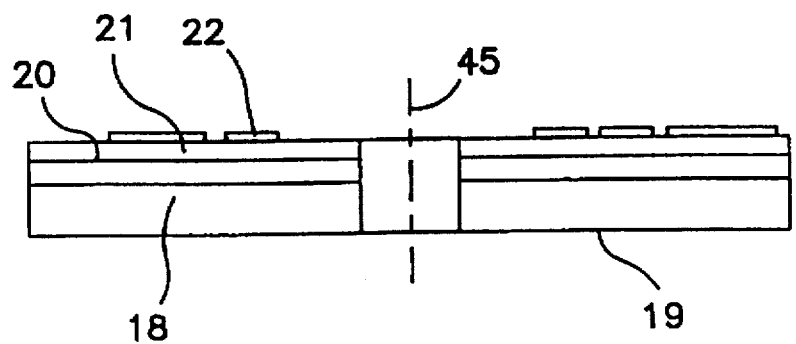
FIG. 2, a cross section through a compact disc along line II—II in FIG. 1.

FIGS. 1 and 2 schematically illustrate the design of a CD 10. The CD 10 comprises different regions in the radial direction as shown in FIG. 1. Looking from the inside out, one can observe the central aperture 11 for centering the CD in the CD player and the inner edge region 12 for clamping the CD in the CD player. A region 13 that carries the identification code and is surrounded by the data region 14 is situated adjacent to the aforementioned inner edge region. Depending on the amount of recorded information, a lead-out 15 or the outer edge region 16 of the CD are situated adjacent to the data region 14.

Viewed in the axial direction from the bottom up (FIG. 2), the CD 10 comprises a transparent polycarbonate layer 18 that is provided with a metal layer 20 on the side situated opposite to the underside 19. Consequently, a reflective surface is created such that the data that is stored within the polycarbonate layer in the form of pits (not shown) can be scanned by optical means in the CD player from the underside 19. A coat of lacquer 21 seals the side of the metal layer 20 that is opposite to the polycarbonate layer 18 with a color layer 22 in the form of a label printed on said coat of lacquer.

Figure 3:
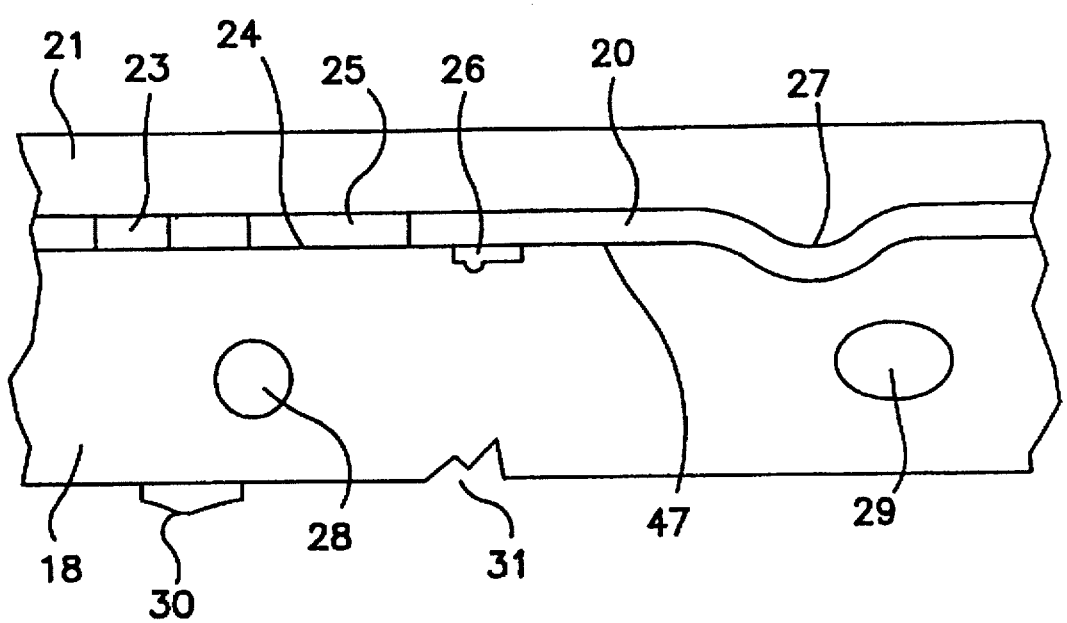
FIG. 3, a schematic representation of the possible defects in a compact disc.

FIG. 3 shows the possible defects that might occur during the manufacture of a CD and that can be displayed by means of conventional measuring methods. Reference numeral 23 identifies so-called pinholes which are caused by dust particles that become located on the surface 24 of the polycarbonate blank, separate from the surface, while the CD is centrifuged during the sputtering process and which entrain a piece of the metal layer 20 during this process. The so-called aluminum scratches 25 are created in the same fashion, but the dust particle initially continues to travel outward on the surface 24. The oil stains 26 represent organic residues on the surface 24 of the polycarbonate layer 18 of the CD 10. A so-called pimple defect 27 is caused by a deformation of the polycarbonate blank 18. Black spots 28 due to inclusions of foreign matter or bubbles 29 due to gas inclusions can also be present within the polycarbonate layer 18. Lacquer splashes 30 or scratches 31 caused by external mechanical influences can occur on the underside 19 of the polycarbonate layer.

These defects diminish the intensity of the test light beam such that black or dark areas become visible at the respective locations of the graphical representation. The other defects which were described previously cannot be easily graphically represented, but partially cause a diminished exposure of the photosensitive receiver or a deflection of the test light beam.

Figure 5A:
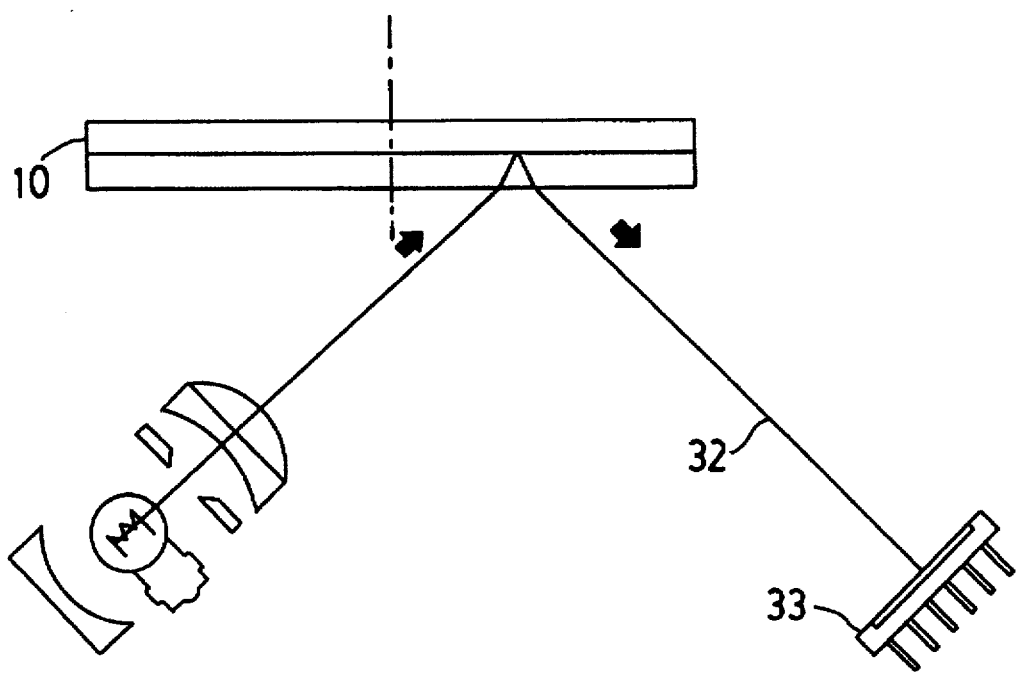
FIG. 5a and 5b, schematic representations of the path of the light beam while testing a deformed CD, FIG. 6, a device according to the invention, and FIG. 7, a different embodiment of a device according to the invention.
Figure 5B:
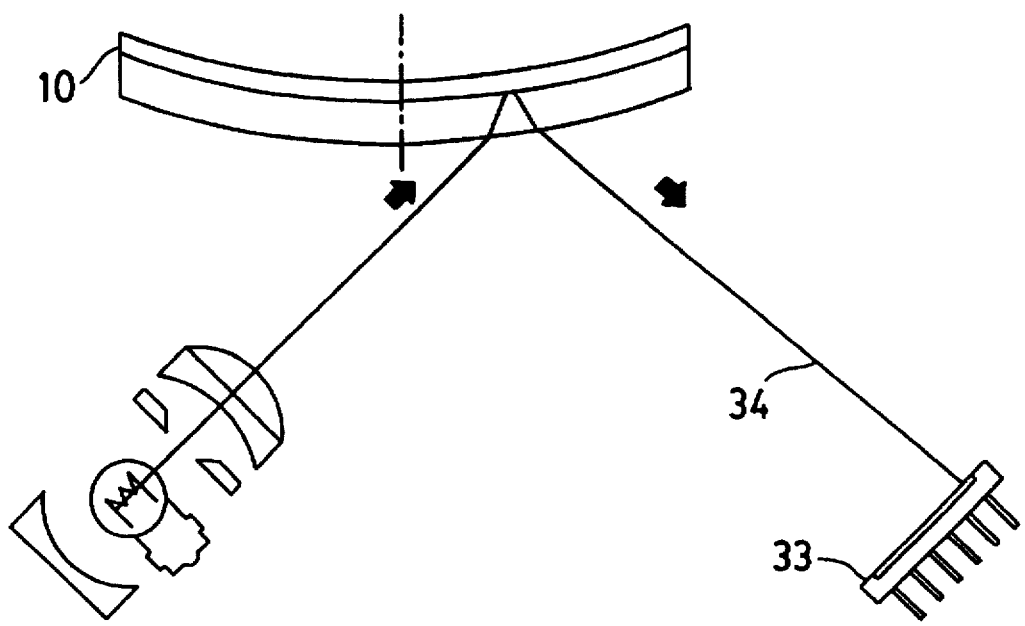

FIGS. 5a and 5b schematically illustrate the path of the light beam when testing a CD for deformations. FIG. 5a shows that the light beam 32 that is reflected by the CD 10 is centrally projected onto the position-sensitive photosensitive receiver 33 if the CD 10 is flat. FIG. 5b shows that the light beam 34 that is reflected by the CD is projected onto the photosensitive receiver further toward the top if the center of the CD 10 is curved downward. The reflected light beam is projected onto the photosensitive receiver 33 further toward the bottom if the CD 10 is deformed in the opposite direction.

Figure 6:
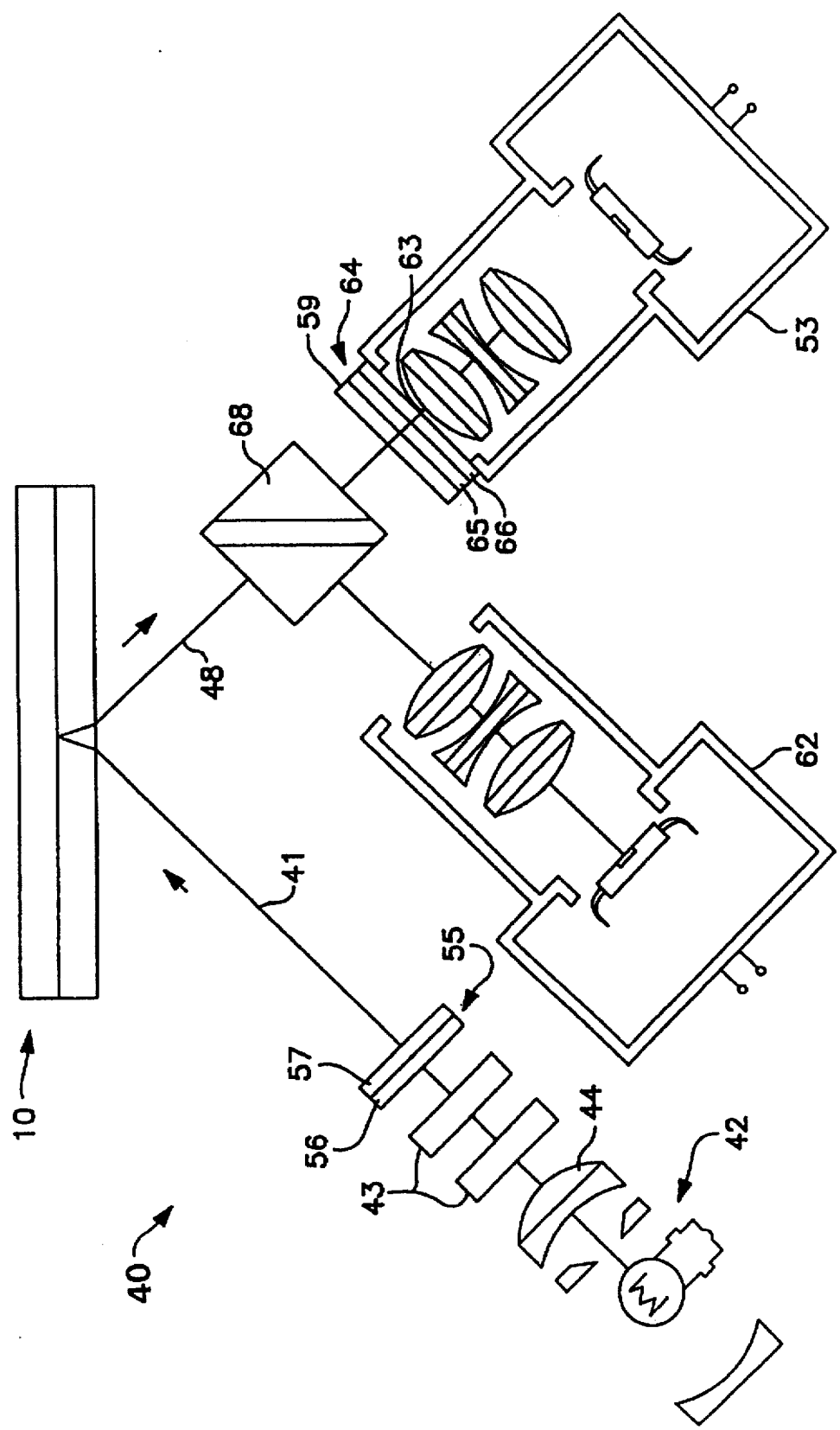

FIG. 6 schematically illustrates a device 40 for carrying out the quality control of CDs 10. This illustration is limited to the path of the light beam 41 because a person skilled in the art is familiar with the required design, the angles to be observed, etc.

Figure 4:
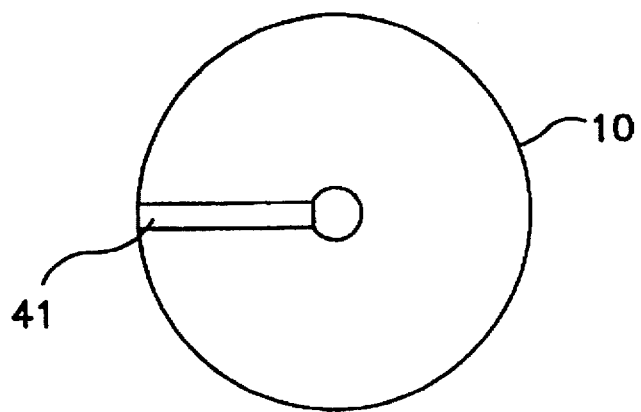
FIG. 4, a top view of a CD that is illuminated by a light beam.

The device 40 comprises a light source 42 that, for example, can be realized in the form of a conventional halogen lamp. A light beam 41 that has a linear shape relative to the surface of the CD 10 and is projected onto the underside 19 of the CD 10, i.e., the reading side, in the form of a beam that originates radially from the central axis 45 can be generated with an arrangement of different, generally known diaphragms and lenses 43, 44. During the test, the CD revolves around this central axis 45. The linear illumination of the CD 10 is illustrated in FIG. 4. Naturally, it is also possible that this light beam extends over the entire diameter of the CD 10. In this case, only one-half revolution of the CD 10 would be required for carrying out a comprehensive test.

The light beam 41 generated by the light source 42 is projected onto the underside 19 of the transparent layer 18 of the CD 10, i.e., the polycarbonate layer, and refracted at this location in accordance with the optical properties of this layer. The angle of incidence α is chosen such that no total reflection occurs on the underside 19 of the polycarbonate layer 18, e.g., between 30° and 60°. However, it is, in principle, also possible for the angle of incidence to be 90°, but an acute angle of incidence α is preferred. The light beam 41 is reflected on the reflective surface 47 formed by the metal layer 20 and, after being refracted correspondingly, emerges from the polycarbonate layer 18 at the same angle of reflection β.

A first photosensitive receiver 53 is arranged in the path of the reflected light beam 48. Depending on the design of the device and the type of defect to be detected, the photosensitive receiver can be realized in the form of a line camera or matrix camera.

A beam splitter 68 that deflects the light beam 48 that was reflected by the reflective surface 47 of the CD 10 toward the second photosensitive receiver 62 is arranged in front of the photosensitive receiver 53. In this embodiment, a polarizing device 55 is arranged in front of the light source 42, with said polarizing device comprising a linear polarizing filter 56 and a phase delay plate 57, e.g., a λ/4 plate, in order to generate circularly or elliptically polarized light within at least one wavelength range. A corresponding polarizing device 64 is installed in the opposite direction in front of the first photosensitive receiver 53, wherein this polarizing device comprises a phase delay plate 65, e.g., a λ/4 plate, and a linear polarizing filter 66. Consequently, this photosensitive receiver 53 is able to display internal stresses independently of the privileged direction of the birefrigence. In addition, a color filter 59 is arranged in front of the phase delay plate 65 viewed in the beam direction so as to attain a high-contrast display and superior measuring accuracy.

Such a polarizing device is, however, not provided in front of the second photosensitive receiver 62, e.g., a line camera, so that the aforementioned clouds can also be displayed in addition to the defects of the first-mentioned group of defects.

Figure 7:
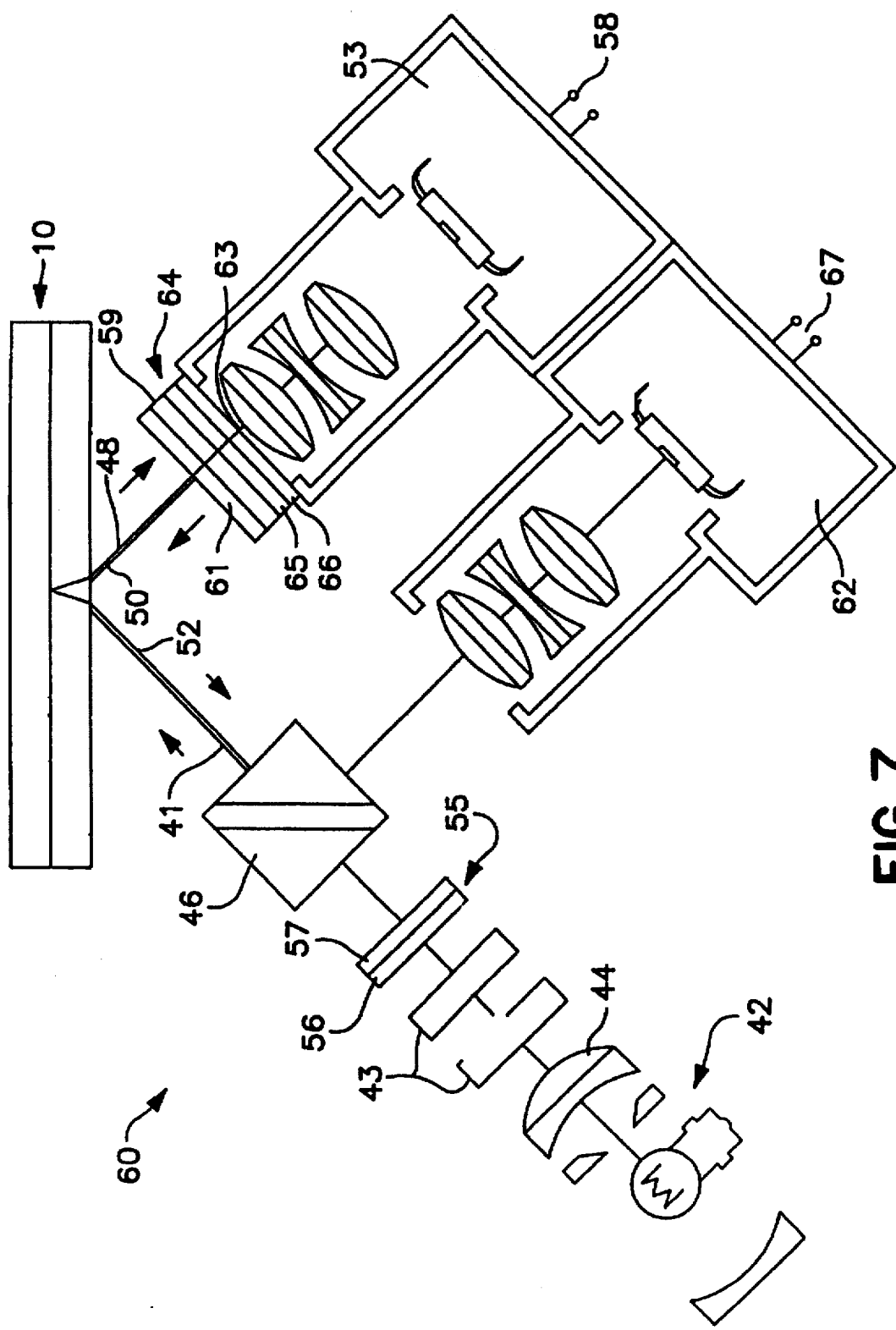

FIG. 7 shows one additional development of this embodiment of the invention which at least partially corresponds to the embodiment according to FIG. 6. Consequently, identical components or elements are identified by the same reference numerals.

In the device 60 shown in FIG. 7, a partially transparent mirror 61 is arranged in front of the photosensitive receiver 53. In this arrangement, the light beam 50 that is reflected by the partially transparent mirror 61 is reflected exactly in the opposite direction such that a light beam 50 that extends opposite to the reflected light beam 48 is created. In order to prevent any misunderstanding, it should be emphasized that the different light beams are only illustrated adjacent to one another for reasons of elucidation. If the optical system is adjusted correctly and the CD 10 is not deformed, the light beams extend at least approximately on top of one another.

This light beam 50 is projected onto the underside 19 of the CD 10 at the same angle as the angle of incidence α (and consequently the angle of reflection β) and is again refracted in accordance with the optical properties of the transparent layer 18. This light beam is also reflected on the reflective surface 47 at approximately the same point 51 at which the incident light beam 41 is reflected. The emerging light beam 52 is projected onto a beam splitter 46 that is arranged between the CD 10 and the light source. The light beam is deflected at this location, e.g., by 90°. In this case, the beam splitter 46 is designed in such a way that the portion of the original light beam 41 which is directly emitted from the light source 42 is not deflected. The second photosensitive receiver 62 is arranged behind the beam splitter 46 viewed in the direction of deflection.

In this embodiment, a polarizing device 55 that comprises a linear polarizing filter 56 and a phase delay plate 57 in order to generate circularly polarized light within at least one wavelength range is arranged in front of the light source 42. A corresponding polarizing device 64 that comprises a phase delay plate 65 and a linear polarizing filter 66 viewed in the beam direction is installed in the opposite direction in front of the photosensitive receiver 53. In addition, a color filter 59, the wavelength of which corresponds to the wavelength of the circularly polarized light, is arranged in front of the phase delay plate 65 as viewed in the beam direction. However, it is also possible to realize the partially transparent mirror in the form of an interference filter, the wavelength of which corresponds to the wavelength of the circularly polarized light. In this case, the color filter 59 is no longer required.

Due to the arrangement according to FIG. 7, the light beam passes over the CD 10 twice, namely once in the form of the original light beam 41 and the second time in the form of the light beam 50 that was reflected by the partially transparent mirror 61, in one measuring position, i.e., the CD 10 does not carry out an additional revolution, before said light beam is projected onto the photosensitive receiver 62. It is quite obvious that this measure makes it possible to display low-contrast defects because the same light beam is decreased twice by the same defect such that the contrast is increased as compared to the adjacently extending undisturbed beams.

In the embodiment according to FIG. 7, it is also possible to interchange the two cameras. If the polarizing device 64 were arranged, for example, in front of the second photosensitive receiver, the advantage of a higher contrast that would be practical for detecting the defects of the first-mentioned group of defects would not obtain because the light beam that exposes the corresponding camera behind the partially transparent mirror only passes over the corresponding location on the CD once.

The video outputs 58, 67 of the photosensitive receivers 53, 62 are connected to a data processing system that makes it possible to graphically illustrate the received measured values, e.g., on a monitor. It is quite obvious that this embodiment in which two cameras are utilized in only one device is able to reliably display several CD defects. This process previously required several devices for testing a CD.

It is practical to provide a more intense light source 42 because the light beam 41 in the aforementioned embodiments is split by the beam splitter 46, 68 and the partially transparent mirror 61.

In the two embodiments according to FIGS. 5 and 6, it is also possible to realize the beam splitter 46, 68 in the form of a polarizing beam splitter. In this case, the λ/4 plate 57 would be arranged behind the beam splitter 46 in order to generate the circularly polarized light. This would mean that a polarizing device is provided in front of both photosensitive receivers. However, the effects of the polarizing beam splitters 46, 68 on the graphical representations must be taken into consideration during the subsequent evaluation.

In addition, it is practical if linearly polarized light is generated in the light source 42, e.g., by utilizing a laser. In this case, a phase delay plate, e.g., λ/4 plate, would suffice for generating circularly or elliptically polarized light within at least one wavelength range.

It is, in principle, possible to detect internal stresses with any type of polarized light. In order to allow the universal utilization of the test method, it is proposed that the polarizing filters which are respectively arranged in front of the light source and in front of the photosensitive receiver be aligned in such a way that the light, preferably the maximum quantity of light, passes if a flawless object is tested such that other defect phenomena can also be observed in the respective photosensitive receiver at the same time as the birefringence. Depending on the significance of possible defects of the object, the line camera or even the matrix camera, for example, can be provided with the corresponding polarizing device.

The previous description primarily referred to the utilization of linearly or circularly polarized light. Naturally, it is also possible to generate elliptically polarized light by correspondingly aligning (turning) the linear polarizing filter and the phase delay plate (e.g., a λ/4 plate) toward one another in front of the light source. This provides the additional advantage that the change in the direction of polarization caused by the metallic reflective layer can be compensated. A change in the direction of polarization caused by the metal reflective layer is a physically known procedure, i.e., the required angle between the linear polarizing filter and the phase delay plate can be easily determined. In this case, turning at a 45° angle is chosen such that possible birefrigences can be displayed independently of the privileged direction. The alignment (turning) of the phase delay plate and the linear polarizing filter in front of the photosensitive receiver is carried out correspondingly. In this case, it is also practical if the respective polarizing devices are aligned in such a way that the light passes if the CD is flawless with respect to the birefrigence caused by the internal stresses.

The figures only show embodiments of devices in which the light beam is reflected by the reflective layer. Naturally, it is also possible to realize a device in which the light beam passes through the transparent blank. In this case, the corresponding photosensitive receivers and the optical means for splitting the light beam would have to be arranged on the side of the CD that is situated opposite to the light source.

I claim:

1. A method for optically testing an optical disc, a compact disc or the like which has a transparent layer, comprising the steps of:
    emitting a light beam from a light source;
    polarizing said light beam with a type of polarization;
    projecting said light beam, after said light beam is polarized, onto the optical disc such that said light beam is reflected by the optical disc;
    splitting said light beam reflected by the optical disc into a first part and a second part;
    exposing said first part of said splitted light beam to a first photosensitive receiver;
    filtering from said second part of said splitted light beam a portion which corresponds in polarization to said type of polarization used to polarize said light beam before said light beam was projected onto the optical disc; and
    exposing said portion of said second part of said splitted light beam to a second photosensitive receiver.

2. Method according to claim 1, wherein said type of polarization is linear polarization.

3. A method according to claim 1, wherein said first photosensitive receiver is a line camera and said second photosensitive receiver is a matrix camera.

4. A method according to claim 1, wherein said first photosensitive receiver is a matrix camera and said second photosensitive receiver is a line camera.

5. Method according to claim 1, wherein light is transmitted to said second photosensitive receiver if an essentially flawless optical disc is tested.

6. Method according to claim 1, wherein said type of polarization is elliptical polarization and wherein at least one wavelength range of the light beam is elliptically polarized during said polarizing step.

7. A method according to claim 6, wherein said portion of said second part of said splitted light beam includes a wavelength range which corresponds to said at least one wavelength range of said light beam which is elliptically polarized during said polarizing step.

8. Method according to claim 1, wherein said type of plarization is circular polarization and wherein at least one wavelength range of the light beam is circularly polarized during said polarizing step.

9. A method according to claim 8, wherein said portion of said second part of said splitted light beam includes a wavelength range which corresponds to said at least one wavelength range of said light beam which is circularly polarized during said polarizing step.

10. Device for optically testing an optical disc, a compact disc or the like which has a transparent layer, comprising:
    a light source capable of emitting a light beam onto the optical disc which is reflected by the optical disc;
    first polarization means located between said light source and the optical disc for polarizing the light beam with a type of polarization before said light beam is projected on the optical disc;

a beam splitter for splitting said light beam reflected by the optical disc into a first part and a second part;

a first photosensitive receiver exposed to said first part of said splitted light beam;

second polarization means for filtering said second part of said splitted light beam, said second polarization means corresponding in polarization-type to said type of polarization of said first polarization means; and a second photosensitive receiver exposed to a portion of said second part of said splitted light beam which filters through said second polarization means.

11. Device according to claim 10, wherein the second polarization means is aligned in front of said second photosensitive receiver such that light is transmitted to said second photosensitive receiver if an essentially flawless optical disc is tested.

12. A device according to claim 10, wherein said first photosensitive receiver is a line camera and said second photosensitive receiver is a matrix camera.

13. A device according to claim 10, wherein said first photosensitive receiver is a matrix camera and said second photosensitive receiver is a line camera.

14. A device according to claim 10, wherein said first polarization means comprises a linear polarization filter and said second polarization means comprises a linear polarization filter.

15. Device according to claim 10, wherein the first polarization means comprises a linear polarizing filter and a phase delay plate in order to elliptically polarize at least one wavelength range of the light beam, and wherein said second polarization means comprises a corresponding phase delay plate and a corresponding linear polarizing filter.

16. Device according to claim 15, further comprising a color filter having a wavelength range which corresponds to said at least one wavelength range of the light beam elliptically polarized by said first polarization means, said color filter being arranged to filter said second part of said splitted light beam.

17. Device according to claim 10, wherein the first polarization means comprises a linear polarizing filter and a $\lambda/4$-plate in order to circularly polarize at least one wavelength range of the light beam, and wherein said second polarization means comprises a corresponding $\lambda/4$-plate and a corresponding linear polarizing filter.

18. A device according to claim 17, further comprising a color filter having a wavelength range which corresponds to said at least one wavelength range of the light beam circularly polarized by said first polarization means, said color filter being arranged to filter said second part of said splitted light beam before said second part is exposed to said second photosensitive receiver.

* * * * *